US 6,651,956 B2
United States Patent
Miller
Date of Patent: Nov. 25, 2003

(54) SLIT-TYPE SWABABLE VALVE (75) Inventor: Pavel T. Miller, St. Peterburg, FL (US)

(73) Assignee: Halkey-Roberts Corporation, St. Petersburg, FL (US)

( * ) Notice: Subject to any disclaimer, the term of this patent is extended or adjusted under 35 U.S.C. 154(b) by 0 days.

(21) Appl. No.: 10/224,887

(22) Filed: Aug. 21, 2002

(65) Prior Publication Data
US 2003/0141477 A1 Jul. 31, 2003

Related U.S. Application Data
(60) Provisional application No. 60/353,711, filed on Jan. 31, 2002.

(51) Int. Cl.[7] ............................................. F16K 51/00
(52) U.S. Cl. ................................. 251/149.1; 604/249
(58) Field of Search ....................... 257/149.1; 604/249, 604/256, 537, 167.02, 167.03, 167.04, 905

(56) References Cited

U.S. PATENT DOCUMENTS

| 3,806,086 A | 4/1974 | Cloyd |
| 4,917,668 A | 4/1990 | Haindl |
| 5,064,416 A | 11/1991 | Newgard et al. |
| 5,080,654 A | 1/1992 | Picha et al. |
| 5,108,380 A | 4/1992 | Herlitze et al. |
| 5,242,393 A | 9/1993 | Brimhall et al. |
| 5,312,362 A | 5/1994 | Pfolsgraf et al. |
| 5,330,435 A | 7/1994 | Vaillancourt |
| 5,349,984 A | 9/1994 | Weinheimer et al. |
| 5,360,413 A | 11/1994 | Leason et al. |
| 5,380,306 A | 1/1995 | Brinon |
| 5,474,536 A | 12/1995 | Bonaldo |
| 5,474,544 A | 12/1995 | Lynn |
| 5,509,433 A | 4/1996 | Paradis |
| 5,509,912 A | 4/1996 | Vaillancourt et al. |
| 5,520,666 A | 5/1996 | Choudhury et al. |
| 5,533,708 A | 7/1996 | Atkinson et al. |
| 5,549,566 A | 8/1996 | Elias et al. |
| 5,616,130 A | 4/1997 | Mayer |
| 5,676,346 A | 10/1997 | Leinsing |
| 5,699,821 A | 12/1997 | Paradis |
| 5,730,418 A * | 3/1998 | Feith et al. ............... 251/149.1 |
| 5,820,601 A | 10/1998 | Mayer |
| 6,036,171 A | 3/2000 | Weinheimer et al. |
| 6,039,302 A * | 3/2000 | Cote et al. ............... 251/149.1 |
| 6,079,432 A * | 6/2000 | Paradis .................... 251/149.1 |
| 6,171,287 B1 * | 1/2001 | Lynn et al. ................. 604/256 |

OTHER PUBLICATIONS

Safe Connect, Winfield Medical, 10 page brochure.
Quality Check Valves from Burron, Burron Medical Inc., one page brochure.
SoloPak Maxcess Needleless System, SoloPak Pharmaceuticals, Inc., two page brochure.
The MMG MLI–Set, MMG Infusion Technologies, one page brochure.
Clave Connector, Clave 1, Rev. 3/94, two page brochure.
Smart Site Needleless System, Alaris Medical Systems Inc., two page brochure, 5/97.

* cited by examiner

Primary Examiner—John Bastianell
(74) Attorney, Agent, or Firm—Trexler, Bushnell, Giangiorgi, Blackstone & Marr, Ltd.

(57) ABSTRACT

A valve which includes a stem having a slit at an end thereof. The valve stem is located in a valve body and is deformable. When a tip of an instrument is engaged with a slit in the stem, the stem shifts in the valve body, top portion folds inward, the slit seals against the instrument and allows liquid to flow through the stem, to or from the instrument. All components have circular cross sectional geometry.

21 Claims, 4 Drawing Sheets

SLIT-TYPE SWABABLE VALVE

RELATED APPLICATION (PRIORITY CLAIM)

This application claims the benefit of U.S. provisional application Ser. No. 60/353,711, filed Jan. 31, 2002.

BACKGROUND

The present invention relates generally to valves, and relates more specifically to a novel valve construction that provides many improved features over the prior art, and is well adapted for medical usage, such as in needleless IV sets, and other medical applications where it is desirable to avoid use of needles in the transmission and delivery of fluid products to patients in a sterile environment.

Presently, there are many types of swabable valves designed to address needlesticks safety issues. Such valves must satisfy many requirements. For example, they must safely withstand, without loss of performance, at least 100 connects and disconnects to an injection site before the set is replaced. In addition, that connection shall be maintained for an extended period of time before disconnection is made. Still, the site shall be capable of accepting subsequent connections without allowing any leakage. Such valves must seal against pressurized fluid within a set. They must withstand pressures in excess of, for example, 25 p.s.i., for a short time, such as during an injection made through an adjacent site or if a pump is nearby. Such valves shall not contain any dead space where fluid can collect and not be readily flushed away. Also, priming volume should be minimized. Furthermore, they must also be easily accessible by standard luer connectors and provide secure locking features, so such connectors could be left connected to the site without further assistance from a practitioner. Further, such valves shall be manufactured at high speeds and low cost. At the same time, the design must allow for minimal manufacturing defects. Still further, it is desirable that such valves have as few components as possible, and be easily assembled, without requiring any difficult component orientation or positioning. Another highly desirable feature is easy and safe swabability of the valve inlet area.

Most current valves restrict free flow of passing fluid by employing narrow passages, ribs or internal cannula-like features. Restricting the flow path in such a manner may create conditions for hemolytic damage. Such restrictions also make the valve generally more difficult to flush. Examples of some valves are shown in U.S. Pat. Nos. 6,325,782 and 6,290,206.

Further, some valves' stems or seals employ an opening that is closed upon assembly. This opening must be produced during molding, and requires a core pin to extend all the way through the part, creating a possibility for flash to develop at the core pin shut off area. Such flash would then be found at the proximal end of the stem and present a possible danger if removed by the action of a penetrating luer connector as this would case the flash to be pushed into the fluid flow path.

Moreover, valves that employ resilient stems with a slit have an elliptical cross sectional geometry and slit orientation must be precisely controlled by positioning system during slit manufacture or during assembly. Examples of this type of valve is shown in U.S. Pat. Nos. 6,050,978 and 5,354,275.

Furthermore, in medical applications, it is usually desirable to prevent the patient from being exposed to the fluid which is being injected to or extracted from the patient, and it is desirable to insulate nurses and doctors from exposure to the liquid which may contain the patient's blood or waste products. However, often the instrument used to inject or withdraw the fluid (which is generally the male component of the syringe), retains some of the fluid on the tip thereof, thus providing a risk to nurses and doctors of being exposed to the fluid. Wiping off this fluid prior to disconnecting the instrument is highly desirable.

Still further, some similar devices currently on the market employ thin ribs or cannula-like housing details, which might be susceptible to breakage. Such breakage could damage the flexible sealing stem in the valve, or the flash could become loose inside the flow path. The same ribs or narrow housing channels present obstacles for smooth fluid flow, thus restricting flow and, in the case of blood transfer, they increase the risk of mechanical hemolytic damage.

The present invention is directed to address at least some of the above-mentioned requirements, as well as undesirable characteristics of some current swabable valves.

OBJECTS AND SUMMARY OF THE DISCLOSURE

A general object of the present invention is to provide a valve that seals itself to restrict fluid flow thereinto, and decreases the risk of contaminants such as bacteria collecting on or within the valve. All external surfaces in the proximity of the valve stem are accessible to be wiped clean with a sterile swab.

Another object of the present invention is to provide a valve which includes a stem that provides a relatively flat and wrinkle-free top surface which can be easily swabbed.

Another object of the present invention is to provide a valve which minimally restricts fluid flow therethrough without requiring fluid to pass narrow cannula like passages and also without any ribs like housing features, to provide valve structure with an unobstructive flow path allowing for smooth fluid flow without hemolytic damage and designed so, it will not present difficulty for molding and high speed assembly.

Still another object of the present invention is to provide a valve structure including a female valve component that seals with a male component or instrument when the instrument is engaged therewith so that there is no leakage of fluid.

Yet another object of the present invention is to provide a valve which automatically wipes or swabs the male component or instrument upon the instrument being disengaged or removed therefrom.

A still yet further object of the present invention is to provide a valve structure, and particularly a female valve that obtains an effective seal and does not have a tendency to leak fluid into the surrounding area upon the male component or instrument being disengaged therefrom.

Yet still another object of the present invention is to provide a valve structure that allows fluid flow in both directions upon a male component or instrument being engaged therewith.

Still another is to provide uniform circular cross sectional geometry for all components so there is no need for precise orientation for the purpose of slitting or assembly. Such construction will allow for highly reliable assembly without employment of sophisticated high speed positioning systems.

Briefly, and in accordance with the above, the present invention envisions a valve or female component that engages with a male component or instrument, where the valve includes a resilient, deformable stem which is located in a valve body and is shiftable therein. The valve stem has a slit, and is uniformly round, as is the housing (i.e., has a uniformly round cross-sectional profile). Additionally, the valve stem includes a circumferential notch on its exterior surface. The notch provides a point of weakness on the exterior surface of the valve stem. The notch is configured to provide that, when the male component or instrument is engaged with the valve, the valve stem buckles or expands generally outwardly, at the notch, thereby providing increased flow volume within the valve stem. When an instrument is engaged in the slit of the valve stem, the stem shifts in the valve body, and the slit seals against the outer surface of the instrument or male member, thus allowing liquid to flow through the stem, to or from the instrument. The structure of the valve is such that when the valve is actuated, fluid can flow in either direction through the valve. As the instrument is being removed from the stem, the slit in the valve stem closes, and this prevents fluid leak upon further removal of the instrument. Also, the stem configuration provides that the stem swabs or cleans the tip of the instrument upon the tip of the instrument being removed from the slit. The stem is further configured with a relieve feature at the proximal end to achieve relatively flat and wrinkle free top surface for an easy swabbing.

BRIEF DESCRIPTION OF THE DRAWINGS

The organization and manner of the structure and function of the invention, together with further objects and advantages thereof, may be understood by reference to the following description taken in connection with the accompanying drawings, wherein like reference numerals identify like elements, and in which.

DESCRIPTION

Figure 5:
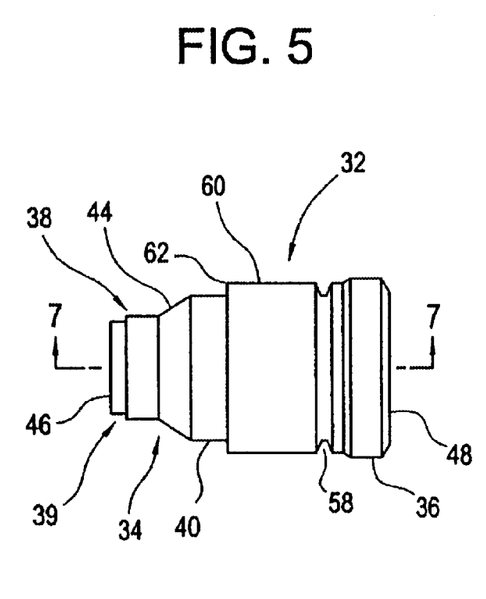
FIG. 5 is an enlarged, side, elevational view of a valve stem component of the valve illustrated in FIGS. 1–4.
Figure 6:
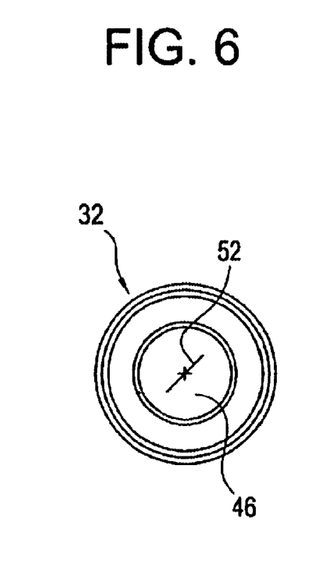
FIG. 6 is an enlarged, top, plan view of the valve stem component illustrated in FIG. 5.
Figure 7:
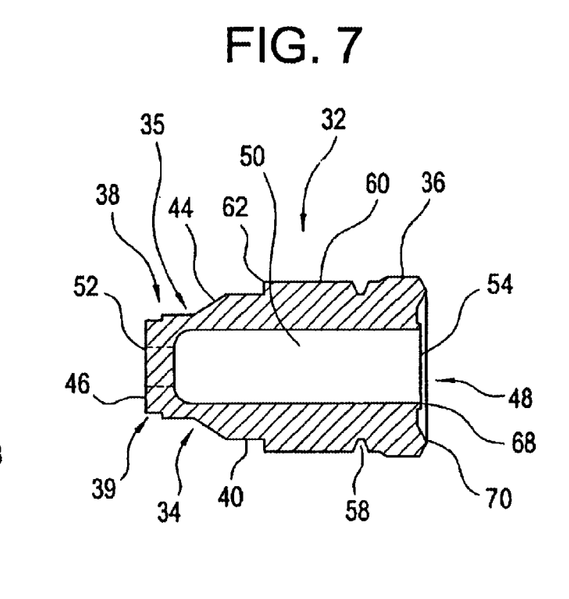
FIG. 7 is an enlarged, cross-sectional view of the valve stem component shown in FIG. 5, taken along line 7—7 of FIG. 5.
Figure 8:
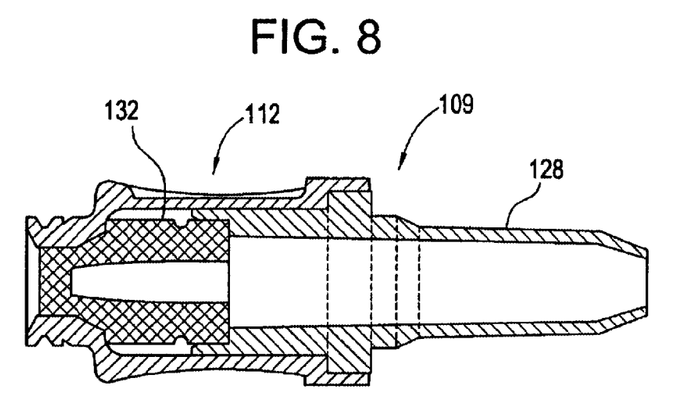
FIG. 8 is an enlarged, cross-sectional view of an alternative valve, similar to the valve shown in FIGS. 3 and 4, but where a back end of the valve is configured for directly receiving a fluid line.
Figure 9:
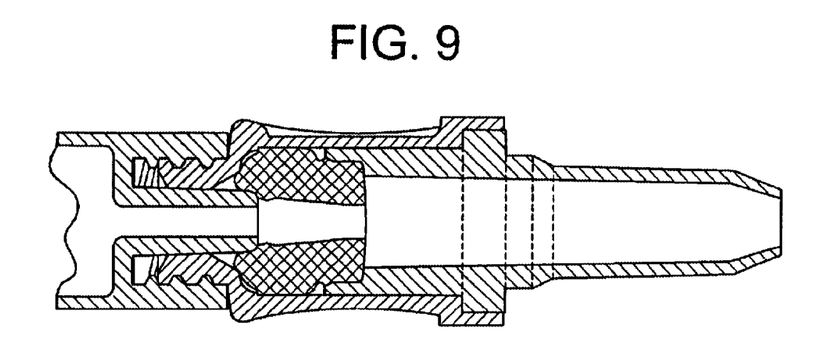
FIG. 9 is an enlarged, cross sectional view, of the valve of FIG. 8, showing an instrument engaged with the valve.

FIGS. 1–4 illustrate a valve that is in accordance with an embodiment of the present invention. FIGS. 5–7 illustrate a valve stem component of the valve in more detail. FIGS. 8 and 9 illustrate an alternative version of the valve shown in FIGS. 1–4, wherein a rear portion of the valve is configured to receive a fluid line. Each of the valves permits flow in either direction and seals to restrict fluid flow therethrough when the male component or instrument is disengaged. Also, each of the valves provides a seal with a tip of an instrument when the tip is engaged therewith and automatically wipes or swabs the tip of the instrument clean upon the instrument being disengaged therefrom. All external surfaces in the proximity of a stem in each of the valves are accessible to be wiped clean with a sterile swab. Further, neither one of the valves exposes an interior neutral area of the valve to the fluid flowing through the valve, since engagement of the instrument tip with the stem deforms and compresses the stem into sealed contact with the valve housing. Further, it does not contain any ribs or cannula like features and all components have round cross sectional geometry. Finally, each of the valves reduces the likelihood that fluid will leak out from the valve into the surrounding environment when the instrument is disengaged therefrom. Therefore, each valve is specifically directed towards alleviating many problems encountered in the prior art, and provides a sterile fluid path for the delivery or withdraws of fluid to or from a patient.

Figure 1:
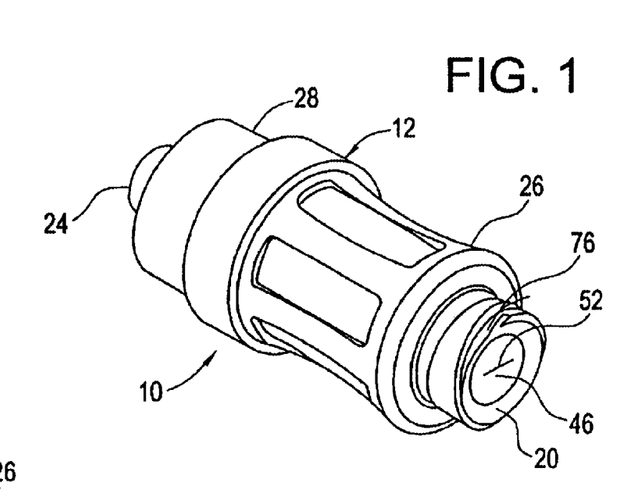
FIG. 1 is an enlarged isometric view of a valve that is in accordance with an embodiment of the present invention.
Figure 2:
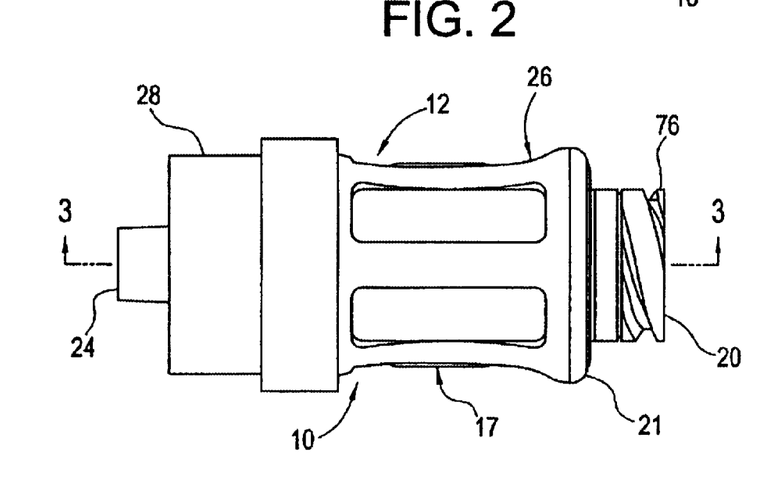
FIG. 2 is an enlarged, side elevational view of the valve shown in FIG. 1.
Figure 3:
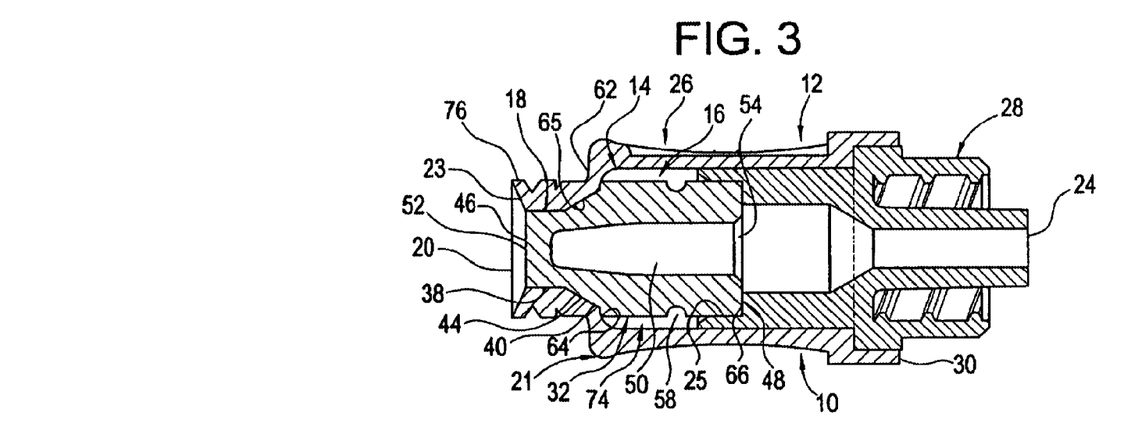
FIG. 3 is an enlarged, cross-sectional view of the valve shown in FIGS. 1 and 2, taken along line 3—3 of FIG. 2.
Figure 4:
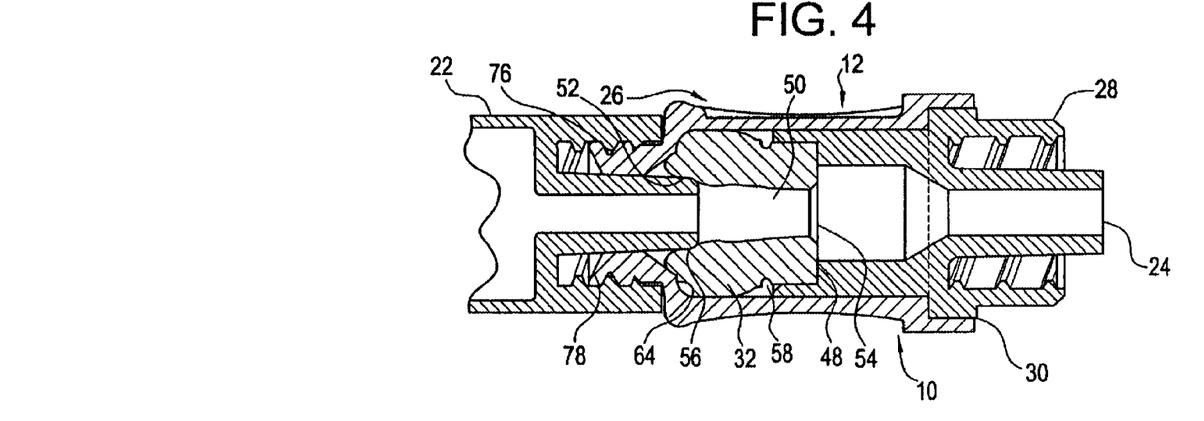
FIG. 4 is an enlarged, cross-sectional view, much like FIG. 3, of the valve of FIGS. 1 and 2, showing an instrument engaged with the valve.

The valve 10 shown in FIGS. 1–4 includes a substantially tubular valve body 12 having, as shown in FIGS. 3 and 4, a central axial bore 14 forming an enlarged diameter section 16 and a reduced diameter section 18. The bore 14 defines a first open end 20 for receiving a male valve component or instrument 22 (see FIG. 4), such as a needleless syringe having a luer tip, and a second open end 24 for communication with a fluid line (not shown). Preferably, the valve body 12 is comprised of a relatively rigid, durable material such as a thermoplastic material.

As shown most clearly in FIGS. 3–4, for ease of assembly, the valve body 12 may be formed of two portions, a front body portion 26 and a back end portion 28, which are ultrasonically sealed together at a weld joint 30 to provide the continuous valve body 12. Ultimately, it should be appreciated that the location of the joint 30 is not imperative, and that the valve body 12 need not even be formed of two separate pieces that are connected together, but may be formed of even more pieces or may be formed as a unitary, single-bodied piece. As an alternative to the weld joint 30, a snap joint or a glued joint may be provided between the front portion 26 and the rear portion 28 of the valve body 12. As shown, preferably the shape of the housing 12 is such that its external surface provides a generally convex-like shape, wherein a shoulder cross sectional diameter at a proximal end is larger than the cross sectional diameter in the middle of the housing (i.e., the housing 26 is wider at shoulder 21 than it is in the middle of the valve 17), thus facilitating secure handling of the valve 10.

As shown in FIGS. 1–4, the rear portion 28 of the valve body 12 may be configured as a male luer fitting for receiving a corresponding female luer fitting (not shown). Alternatively, as shown in FIGS. 8 and 9, the rear portion may be configured for direct engagement with a fluid line. In fact, there are many alternatives for the shape and configuration of the rear end of the valve.

Within the valve body 12 is a valve stem 32. Preferably, the stem 32 is comprised of silicone, but the stem 32 may instead be formed of some other resilient elastomer material, such as natural rubber, a thermoplastic elastomer, or a thermoplastic rubber. As shown in FIGS. 3, 5, and 7, the stem 32 preferably has a generally conical front body portion 34 and a generally cylindrical rear body or throat portion 36. Both the front body portion 34 and throat portion 36 have generally circular cross-sectional profiles, and the valve body 12 is correspondingly shaped. The front body portion 34 of the stem 32 includes a plurality of generally cylindrical portions 38, 39 and 40 and a generally conical portion 44 which provides that the front body portion 34 generally tapers to an end 46.

Preferably, the valve 10 is configured such that it does not contain any thin ribs or cannula-type details, as this type of structure is often susceptible to breakage, and such breakage could damage the flexible stem 32 or could become loose in the flow path.

The rear body portion 36 of the stem 32 is preferably substantially cylindrical to provide strong axial compression resistance, and terminates at a blunt or flat end 48, generally opposite end 46. As shown in FIGS. 3, 4 and 7, the stem 32 has a central axial fluid passageway 50 therethrough which defines, at one end of the passageway 50, a slit 52 in the end surface 46 of the stem 32 and defines, at the other end of the passageway, an opposite, second end opening 54. As shown in FIG. 4, preferably the second end 54 of the stem 32 aligns with an internal surface of the valve body 12 thus providing a smooth fluid flow path between the fluid passageway 50 in the stem 32 and the valve body 12 for carrying a liquid, air or other fluid within the valve 10. Preferably, the sidewall of the stem 32 extends from one end 46 of the stem 32 to the other 54, and has a circular, successively larger cross-sectional profile along its length.

The cylindrical portion 39 is configured such that it functions as a relieve feature, it allows portion 38 to be fully compressed to resist back pressure and cylindrical portion 39 to be partially compressed to allow end 46 of stem 32 to form a relatively flat and wrinkle free surface.

While the second end opening 54 of the stem 32 is always open, the slit 52 in the front portion 34 of the stem 32 is normally closed. As shown in FIGS. 6 and 7, even when the valve stem 32 is not engaged with the valve body 12, the slit 52 is closed. In other words, the front body portion 34 of the stem 32 need not engage any internal surface of the valve body 12 in order for the slit 52 to close, as the slit 52 is normally closed. Nevertheless, as shown in FIG. 4, the slit 52 can be opened by engaging a tip 56 of an instrument 22 therewith, such as the tip of a needleless syringe.

As shown in FIGS. 3,4,5 and 7, the valve stem 32 includes a circumferential notch 58 on its exterior surface. The notch 58 provides a point of weakness on the exterior surface 60 of the valve stem 32. The notch 58 is configured to provide that, when the male component or instrument 22 is engaged with the valve 10 (see FIG. 4), the valve stem 32 buckles or expands generally outwardly, at the notch 58, thereby providing increased flow volume within the valve stem 32. The increased flow volume provides that there is less flow resistance. When an instrument 22 is engaged in the slit 52 of the valve stem 32, the slit 52 seals against the outer surface of the instrument or male member 22 and the stem 32 shifts in the valve body 12. When the slit 52 is opened, fluid flow is allowed through the stem 32, to or from the instrument 22. The structure of the valve 10 is such that when the valve 10 is actuated, fluid can flow in either direction through the valve 10. As the instrument 22 is being removed from the slit 52 in the end 46 of the stem 32, the slit 52 closes shut, and this prevents fluid leak upon further removal of the instrument 22. Also, the stem configuration is such that the slit 52 swabs or cleans the tip 56 of the instrument 22 as the tip 56 is being removed.

A shoulder 62 is provided on the stem 32, generally at the juncture of the generally conical front body portion 34 and the generally cylindrical portion 36. As shown in FIGS. 3 and 4, the shoulder 62 could engage a corresponding shoulder 64 in the valve body 12, thereby forming a point of sealed contact therebetween.

As shown in FIGS. 3 and 4, this point of sealed contact remains regardless of whether an instrument 22 is engaged with the valve 10 or not. Furthermore, when an instrument 22 is not engaged with the valve 10, and the valve is as shown in FIG. 3, generally the entire side surface of the front portion 34 of the stem 32 sealingly engages internal surface 65 of the valve housing 12. This sealed engagement results from the fact that the taper angle of the front portion 26 of the valve body 12 is generally about the same as that of the front portion 34 of the stem 32.

The end 48 of the stem 32 is also seated against a shoulder 66 within the valve body 12, such an on the interior of the back portion 28, thereby forming another point of sealed contact. To provide for exceptional sealed contact, the end 48 of the stem 32 is provided with both a flat portion 68 adjacent the end 54 and a lip 70 which protrudes from the end 54. While the lip 70 and portion 68 seals against the shoulder 66 within the valve body 12, the portion 36 seals against an adjacent internal side wall 25 within the valve body 12 thereby providing essentially two contact surfaces between the end 48 of the stem 32 and the valve body 12. Hence, overall, there are always essentially three points of sealing contact between the valve stem 32 and the interior of the valve body 12, i.e. a point of sealed contact between shoulder 62 and shoulder 64, and two points of sealed contact between the end 48 of the stem 32 and the interior of the valve body 12. Still further, as discussed above, preferably the angle of taper of the front portion 26 of the valve body 12 is generally about the same as that of the front portion 34 of the stem 32, thereby providing that the surface of the front portion 34 of the stem 32 generally seals against the interior surface 65 of the valve body 12 (see FIG. 3). One having ordinary skill in the art may recognize still other ways in which to provide points of sealed contact between the stem 32 and the valve body 12. Providing sealed contact between the stem 32 and the valve body 12 is important in order to prevent fluid from entering or leaking into the neutral space 74 between the stem 32 and the valve body 12 from the fluid flow area.

When there is no instrument engaged with the valve (as shown in FIGS. 1–3), the slit 52 in the end 46 of the valve stem 32 is fully closed, and the end 46 of the valve stem 32 is generally flush with, or projects axially slightly past, the bottom of the front convex area 23 of the valve body 12, thereby providing that the end 46 of the stem 32 and adjacent areas can be cleaned. This feature is important in medical applications where bacteria growth is to be avoided. To this end, a sterilizing swab can be used to clean the end 46 of the stem 32 and adjacent areas. Convex area 23 helps to guide an instrument 22 into the valve.

The stem 32 is preferably configured such that, when an instrument 22 is not engaged with the valve 10 (as shown in FIGS. 1–3), the valve stem 32 naturally rests in the position shown in FIG. 3. However, means may be provided for urging the end 46 of the stem 32 towards the end 20 of the valve body 12. Particularly, a compression spring (not shown) may be provided in the neutral space 74 between the stem 32 and the valve body 12. To this end, the stem 32 may be provided with an outwardly extending shoulder on the front body portion 34 for engaging an end of the compression spring, and the valve body 12 may be provided with a shoulder for engaging the other end of the compression spring. In this manner, the compression spring can compress between the stem 32 and the valve body 12 and urge the end 46 of the stem 32 towards the end 20 of the valve body 12. Compression would result from the tip 56 of the instrument 22 being inserted into the slit 52 at the end 46 of the stem 32. FIGS. 1–3 show the valve 10 when the tip 56 of the instrument 22 is not so engaged, and FIG. 4 shows the valve 10 when the tip 56 of the instrument 22 is engaged therewith. At either time, the compression spring would tend to restore itself to its free length, but would only be able to reach a pre-loaded state.

Should a compression spring be provided between the stem 32 and the valve body 12, it becomes even more important to prevent fluid from leaking into the neutral space 74 between the stem 32 and the valve body 12 from the fluid flow area. Leaking of fluid into the neutral space 74 can cause a compression spring to corrode or leach metallic components over time, and subsequently the corrosion or leached metals can escape back into the fluid flow area mixing with the flowing fluid. Or, within a medical application, leaking of fluid into the neutral space 74 can cause bacteria to collect on the compression spring, and subsequently the bacteria can escape back into the fluid flow area mixing with the flowing fluid and exposing a patient thereto.

Instead of providing a compression spring between the stem 32 and the valve body 12, it is preferred that the rear body portion 36 of the stem 32 be provided as having a thick wall and being robust enough to provide a sufficient spring rate or force in order to urge the end 48 of the stem 32 towards the first end 20 of the valve body 12.

Operation of the valve 10 shown in FIGS. 1–4 will now be described in connection with engagement of an instrument 22 therewith. As mentioned, the instrument 22 to be engaged with the valve 10 may be a needleless syringe having a luer tip. Before the instrument 22 is engaged with the valve 10, the valve 10 is in the condition shown in FIGS. 1–3. At that time, the slit 52 is closed and hermetically sealed. Additionally, as described above, the stem 32 is sealed against the valve body 12 at various points (i.e., vis-a-vis end 48, shoulder 62, and the entire surface of the front portion 34 of the stem 32).

When the tip 56 of the instrument 22 is first brought into engagement with the slit 52 in the end 46 of the stem 32, the slit 52 initially resists the insertion thereof. However, as the tip 56 of the instrument 22 is further pushed or engaged into the slit 52, the slit 52 eventually deforms or opens to allow entry of the tip 56 of the instrument 22, as shown in FIG. 4, and due to the resiliency of stem 32, a tight hermetic seal is formed between the stem 32 and the tip 56 of the instrument 22. The engagement of the tip 56 with stem 32 serves to compress the stem 32 and further enhance the internal seals, especially at end 54.

As the tip 56 of the instrument 22 is further pushed into the slit 52 in the stem 32, the end 46 of the stem 32 is pushed generally into the valve body 12, and, as shown in FIG. 4, the valve stem 32 buckles or expands generally outwardly, at the notch 58. End 46 of stem 32 collapses and folds inward into the cavity 50, approximately around a fulcrum point 35 located at the area of minimal wall thickness. The slit 52 fully opens and fluid flow is allowed through the stem 32, to or from the instrument 22. As the instrument 22 is being removed from the slit 52 in the end 46 of the stem 32, the slit 52 closes shut, and this prevents fluid leak. Additionally, the stem 32 wipes or swabs the tip 56 clean upon removals.

As shown in FIGS. 1–4, a female thread or luer lock thread 76 may be provided on the valve body 12 near the end 20 thereof for engagement with a corresponding male Luer lock thread 78 on the instrument 22. Or, other corresponding structure may be provided between the valve 10 and the instrument 22 for engagement therebetween. It is preferable to provide the described luer lock threads or some other engagement structure because the engagement between the valve 10 and the instrument 22 helps to align the instrument 22 while providing a mechanical advantage to overcome the resistance by the slit 52 to expanding and accommodating the tip 56 of the instrument 22. However, it should be pointed out that threaded engagement between the valve body 12 and the instrument 22 is not necessary to keep the tip 56 of the instrument 22 and the slit 52 of the stem 32 engaged because the grip or the frictional engagement between the tip 56 of the instrument 22 and section 18 of the valve body 12, plus engagement of the slit 52 around the tip 56, is sufficient to hold the instrument 22 and the valve 10 in engagement. Nevertheless, it may be desirable to provide the above-described luer lock threads 76 and 78 on the instrument 22 and valve body 12, respectively, or some other engagement structure, when large separation forces will be present therebetween. This, of course, will depend on the application in which the valve 10 is used.

After the tip 56 of the instrument 22 is engaged with the slit 52, fluid may be injected or withdrawn via the tip 56 through the stem 32, that is to say, the instrument 22 may suction or inject fluid through the stem 32. As the fluid flows, no fluid enters the neutral space 74 between the stem 32 and the valve body 12. Therefore, bacteria growth in the neutral space 74 is not encouraged.

Consideration is now directed to what occurs upon disengagement of the instrument 22 from the valve 10. As the tip 56 of the instrument 22 is initially withdrawn from the slit 52 in the end 46 of the stem 32, the stem 32, due to its inherent resiliency, is urged toward the end 20 of the valve body 12. As a result of this bias of the stem 32 toward the tip 56, the slit 52 in the stem 32 and adjacent internal stem walls wipe or swab the tip 56 virtually free of fluid as the tip 56 is being withdrawn. In medical applications, this can reduce the waste of expensive injectable solutions and minimize unintended, undesired human exposure to the fluid, which may be contaminated or be a biohazardous fluid.

The above-described valve 10 provides several advantages over the prior art. For example, the neutral space 74 is sealed away from the fluid flow. Therefore, there is no leaking of fluid thereinto, and a compression spring, if provided between the stem 32 and the valve body 12, is not exposed to the flowing fluid. Also, the tip 56 of the instrument 22 is wiped virtually free of fluid upon the tip 56 being withdrawn from the valve 10. Additionally, the valve 10 provides no perceptible areas for bacterial growth. Still further, the stem 32 is configured with a relieve feature 39 to achieve relatively flat and wrinkle free top surface at the end 46. All the components have circular cross sectional geometry and therefor there is no need for precise part orientation during assembly of the valve, allowing for reliable high-speed manufacture. Still further, the stem 32 is configured to buckle when the tip 56 of an instrument 22 is inserted in the slit 52 in the end 46 of the stem 32, and this provides increased internal flow volume and less resistance to fluid flow. Many more advantages are provided by the present invention and have been previously described herein. One having ordinary skill in the art may readily realize even more advantages.

While an embodiment of the present invention is shown and described, it is envisioned that those skilled in the art may devise various modifications of the present invention without departing from the spirit and scope of the foregoing disclosure.

For example, FIGS. 8 and 9 illustrate a valve 10a which is very much like the valve 10 shown in FIGS. 1–4 and described above. The valve 10a, like valve 10, includes a valve body 112 and a stem 132, and operates in much the same fashion. Valve 10a differs from valve 10 in that the back portion 128a of the valve 10a is configured for direct engagement with the fluid line. Still other variations of valve 10 (and valve 10a) are entirely possible.

I claim:

1. A slit-type swabable valve comprising: a valve body having an end; and a resilient, deformable valve stem which is located in said valve body and is shiftable therein, said valve stem having a first end, a second end opposite said first end and an exterior surface, said valve stem having a linear slit at said first end and having a notch on said exterior surface, said notch providing a point of weakness, said notch configured to provide that, when the valve stem shifts in the valve body upon actuation of the valve, the valve stem buckles generally outwardly, at the notch, thereby providing increased flow volume within the valve stem, wherein said first end of said valve stem is proximate said end of said valve body when said valve stem is not shifted, such that said first end of said valve stem is readily accessible for cleaning, wherein said second end of said valve stem is engaged inside said valve body such that said second end does not shift during actuation of the valve, wherein the valve does not include an internal cannula which engages said valve stem, and wherein said slit in said valve stem is normally closed.

2. A slit-type swabable valve as recited in claim 1, wherein both the valve body and valve stem are uniformly round and have a uniformly round cross-sectional profile.

3. A slit-type swabable valve as recited in claim 1, wherein the notch on the valve stem comprises a circumferential notch.

4. A slit-type swabable valve as recited in claim 1, wherein the valve is configured to be actuated via engagement with a male component or instrument, wherein when the valve is actuated, the valve stem shifts in the valve body, and the slit of the valve stem seals against an outer surface of the male component or instrument, thus allowing liquid to flow through the valve stem.

5. A slit-type swabable valve as recited in claim 1, wherein the valve is configured such that when the valve is actuated, fluid is flowable in either direction through the valve.

6. A slit-type swabable valve as recited in claim 1, wherein the valve is configured such that when the valve is not actuated, the slit in the valve stem is closed, thereby preventing fluid from leaking into or out of an end of the valve stem.

7. A slit-type swabable valve as recited in claim 1, wherein the valve is configured to be actuated via engagement with a male component or instrument, and wherein the valve stem is configured to swab or cleans a tip of the male component or instrument upon the tip being removed from the slit.

8. A slit-type swabable valve as recited in claim 1, wherein the valve includes a fluid flow area and neither the valve body nor the valve stem includes any ribs which are disposed in the fluid flow area.

9. A slit-type swabable valve as recited in claim 1, wherein the end of the stem is flat and wrinkle-free.

10. A slit-type swabable valve as recited in claim 1, wherein said valve body has an end which provides an opening in which sits the valve stem, said end of said valve body providing a convex area which leads into the valve.

11. A slit-type swabable valve comprising: a valve body having an end; and a resilient, deformable valve stem which is located in said valve body and is shiftable therein, said valve stem having a first end, a second end opposite said first end, and an exterior surface, said valve stem having a linear slit at said first end and having a notch on said exterior surface, said notch providing a point of weakness, said notch configured to provide that, when the valve stem shifts in the valve body upon actuation of the valve, the valve stem buckels generally outwardly, at the notch, thereby providing increased flow volume within the valve stem, wherein the valve stem is configured to collapse and fold inward generally about a fulcrum point which is located at an area of minimal wall thickness, wherein said first end of said valve stem is proximate said end of said valve body when said valve stem is not shifted, such that said first end of said valve stem is readily accessible for cleaning, wherein said second end of said valve stem is engaged inside said valve body such that said second end does not shift during actuation of the valve, wherein the valve does not include an internal cannula which engages said valve stem, and wherein said slit in said valve stem is normally closed.

12. A slit-type swabable valve as recited in claim 11, wherein both the valve body and valve stem are uniformly round and have a uniformly round cross-sectional profile.

13. A slit-type swabable valve as recited in claim 11, wherein the notch on the valve stem comprises a circumferential notch.

14. A slit-type swabable valve as recited in claim 11, wherein the valve is configured to be actuated via engagement with a male component or instrument, wherein when the valve is actuated, the valve stem shifts in the valve body, and the slit of the valve stem seals against an outer surface of the male component or instrument, thus allowing liquid to flow through the valve stem.

15. A slit-type swabable valve as recited in claim 11, wherein the valve is configured such that when the valve is actuated, fluid is flowable in either direction through the valve.

16. A slit-type swabable valve as recited in claim 11, wherein the valve is configured such that when the valve is not actuated, the slit in the stem is closed, thereby preventing fluid from leaking into or out of an end of the valve stem.

17. A slit-type swabable valve as recited in claim 11, wherein the valve is configured to be actuated via engagement with a male component or instrument, and wherein the valve stem is configured to swab or cleans a tip of the male component or instrument upon the tip being removed from the slit.

18. A slit-type swabable valve as recited in claim 11, wherein the valve includes a fluid flow area and neither the valve body nor the valve stem includes any ribs which are disposed in the fluid flow area.

19. A slit-type swabable valve as recited in claim 11, wherein the end of the stem is flat and wrinkle-free.

20. A slit-type swabable valve as recited in claim 11, wherein said valve body has an end which provides an opening in which sits the valve stem, said end of said valve body providing a convex area which leads into the valve.

21. A slit-type swabable valve comprising: a valve body having an end: and a resilient, deformable valve stem which is located in said valve body and is shiftable therein, said valve stem having a first end, a second end opposite said first end, and an exterior surface, said valve stem having a linear slit at said first end and having a notch on said exterior surface, said notch providing a point of weakness, said notch configured to provide that, when the valve stem shifts in the valve body upon actuation of the valve, the valve stem buckles generally outwardly, at the notch, thereby providing increased flow volume within the valve stem, wherein the valve stem collapses and folds inward generally about a fulcrum point which is located at an area of minimal wall thickness, wherein both the valve body and valve stem are uniformly round and have a uniformly round cross-sectional profile, wherein said first end of said valve stem is proximate said end of said valve body when said valve stem is not shifted, such that said first end of said valve stem is readily accessible for cleaning, wherein said second end of said valve stem is engaged inside said valve body such that said second end does not shift during actuation of the valve, wherein the valve does not include an internal cannula which engages said valve stem, and wherein said slit in said valve stem is normally closed.

* * * * *